US011773037B2

(12) United States Patent
Fickel et al.

(10) Patent No.: US 11,773,037 B2
(45) Date of Patent: Oct. 3, 2023

(54) DISTRIBUTION HUB FOR C4 CONVERSION TO ETHANE/PROPANE FEEDSTOCK NETWORK

(71) Applicant: SABIC Global Technologies B.V., Bergen op Zoom (NL)

(72) Inventors: Dustin Fickel, Sugar Land, TX (US); Ramakumar Allada, Sugar Land, TX (US); Kaushik Gandhi, Sugar Land, TX (US); Uwaidh Al-Harethi, Riyadh (SA); Robert Broekhuis, Sugar Land, TX (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 102 days.

(21) Appl. No.: 17/593,006

(22) PCT Filed: Feb. 27, 2020

(86) PCT No.: PCT/IB2020/051690
§ 371 (c)(1),
(2) Date: Sep. 3, 2021

(87) PCT Pub. No.: WO2020/178683
PCT Pub. Date: Sep. 10, 2020

(65) Prior Publication Data
US 2022/0177391 A1 Jun. 9, 2022

Related U.S. Application Data

(60) Provisional application No. 62/814,093, filed on Mar. 5, 2019.

(51) Int. Cl.
*C07C 4/06* (2006.01)
*C01B 3/34* (2006.01)
*C01B 3/38* (2006.01)

(52) U.S. Cl.
CPC .............. *C07C 4/06* (2013.01); *C01B 3/346* (2013.01); *C01B 3/384* (2013.01); *C01B 2203/0216* (2013.01); *C01B 2203/062* (2013.01)

(58) Field of Classification Search
CPC .......... C07C 4/06; C10G 65/18; C10G 65/10; C10G 47/20
See application file for complete search history.

(56) References Cited

U.S. PATENT DOCUMENTS

| 3,385,782 A | 5/1968 | Buss |
| 3,389,075 A | 6/1968 | Addison |

(Continued)

FOREIGN PATENT DOCUMENTS

| WO | WO 2012/071137 | 5/2012 |
| WO | WO 2017/101985 | 6/2017 |

OTHER PUBLICATIONS

Gao, et. al., "Shale Gas Process and Supply Chain Optimization" *Advances in Energy Systems Engineering.* 2017 pp. 21-46.

(Continued)

*Primary Examiner* — Sharon Pregler
(74) *Attorney, Agent, or Firm* — Norton Rose Fulbright US LLP

(57) ABSTRACT

A process for producing light alkanes and creating a flexible distribution system for those alkanes and related systems are disclosed. The process can include supplying a butane feed stream to a butane conversion unit to produce a light alkane output stream including at least methane, ethane, propane, and hydrogen, separating at least part of the light alkane output stream into separate streams of methane, ethane, and propane and distributing the separated streams as desired. The distribution of the separated streams can include sending the separated ethane and propane streams to downstream processing units which use them as feedstock. The butane (Continued)

containing feed and/or unreacted butane feed can include isobutane, which can be converted to n-butane and then further processed.

13 Claims, 5 Drawing Sheets

(56) References Cited

U.S. PATENT DOCUMENTS

| | | | |
|---|---|---|---|
| 4,061,690 A | | 12/1977 | Bernard et al. |
| 4,140,621 A | * | 2/1979 | Franck .................. C07C 4/06 208/68 |
| 4,522,708 A | | 6/1985 | Leclercq et al. |
| 6,212,891 B1 | | 4/2001 | Minta et al. |
| 6,541,524 B2 | | 4/2003 | O'Rear et al. |
| 2005/0155382 A1 | | 7/2005 | Ohara et al. |
| 2006/0135840 A1 | * | 6/2006 | Reyneke .................. C07C 7/167 585/809 |
| 2010/0158792 A1 | * | 6/2010 | Drnevich .................. C10K 3/04 252/373 |
| 2012/0180502 A1 | * | 7/2012 | Morris .................. F17C 11/007 62/47.1 |
| 2013/0036671 A1 | | 2/2013 | Saccheri et al. |
| 2014/0171704 A1 | * | 6/2014 | Erisken .................. C10G 55/04 585/303 |
| 2016/0362617 A1 | | 12/2016 | Oprins et al. |
| 2016/0369180 A1 | | 12/2016 | Ward et al. |
| 2017/0342334 A1 | | 11/2017 | Oprins et al. |
| 2017/0369795 A1 | * | 12/2017 | Oprins .................. C10G 47/20 |

OTHER PUBLICATIONS

International Search Report and the Written Opinion of PCT/IB 20/51690 dated Jun. 19, 2020.

* cited by examiner

US 11,773,037 B2

DISTRIBUTION HUB FOR C4 CONVERSION TO ETHANE/PROPANE FEEDSTOCK NETWORK

CROSS REFERENCE TO RELATED APPLICATIONS

This application is a national phase application under 35 U.S.C. § 371 of International Application No. PCT/IB2020/051690 filed Feb. 27, 2020, which claims the benefit of priority of U.S. Provisional Patent Application No. 62/814,093 filed Mar. 5, 2019, all of which are hereby incorporated by reference in their entirety.

FIELD OF INVENTION

The present invention generally relates to a process for conversion of butane into light alkanes such as propane, ethane, and methane. More specifically, the present invention concerns a process that contains a butane conversion unit, which is capable of converting butane into propane, ethane, and/or methane. The produced propane, ethane, and/or methane can be sent to a distribution network that distributes the propane, ethane, and/or methane to downstream asset(s) in need of each compound. This set up allows the butane conversion unit and the distribution network to be operated independent of the downstream asset(s) and to supply such downstream asset(s) with the desired compound as needed. The process also allows for enrichment of n-butane in the feed for the butane conversion unit by isomerizing isobutane to n-butane.

BACKGROUND OF THE INVENTION

Butane, propane, ethane, and methane are used extensively in petroleum refining and the chemical industry as part of the process to make natural gas, various fuels, distillates, naphtha, gasoline, gasoline additives, and other refined products such as plastics and catalysts. Butane, propane, ethane, and methane streams are also used as fuel. Typically, ethane and propane are particularly useful chemicals because they can be converted to higher valued products of ethylene and propylene, respectively. Ethane is typically used to make ethylene because it generates a higher yield of ethylene than when using heavier hydrocarbons as feedstock. Propane is also an important chemical used as feedstock to generate propylene, which is also used to produce commodity chemicals and plastics. Butane isomers are also used in different processes and as different products. Isobutane, which can be used as fuel, a refrigerant, a propellant, or used to produce isobutylene, has a higher value than n-butane, which can be used as fuel or to produce butene, propane, ethane, or methane.

Light alkanes can be obtained from a C4 stream through steam cracking, hydrocracking reactions, and/or through hydrogenolysis reactions. However, steam cracking of a butane feedstock produces relatively low yield of ethylene. Processes based on hydrocracking and/or hydrogenolysis reactions can produce a more favorable product composition. In some instances hydrogenolysis reaction can be advantageous. However hydrogenolysis reactions suffer in that they generally cannot effectively convert isobutane, and butane streams commonly available in industry often include both n-butane and isobutane.

Some attempts to increase the yield of C2 and C3 hydrocarbons from butane feedstocks include the use of hydrocracking systems and recycling of the unreacted feed to the hydrocracking unit. By way of example, WO 2012071137 to Bakker et al. describes providing n-butane or isobutane to a hydrocracker to react with hydrogen to produce predominately ethane and recycling the uncracked material back to the reactor. In another example, WO 2017101985 to Oprins describes producing C2 and C3 hydrocarbons from a middle distillate using a hydrocracking process and recycling the resulting streams to enrich the production of C2 and C3 hydrocarbons.

Steam crackers are generally dedicated to a single specific feedstock (e.g., ethane, propane, or butane) and cannot readily accept feedstocks with different or fluctuating compositions. Market conditions fluctuate, and a particular produced feedstock may be in higher demand in different downstream units one day than the next. Nonetheless, in many of the above mentioned methods, the hydrocracking process is tied to a specific steam cracker, furnace, or downstream section which is dedicated to a single specific feedstock.

While various attempts to produce C2 and C3 hydrocarbons from C4 and higher feedstocks, there is little or no flexibility in the utilization of different feedstocks produced or feedstock amount from the hydrocracking and/or hydrogenolysis system, which can create inefficiencies in the system and missed economic opportunities.

BRIEF SUMMARY OF THE INVENTION

A solution to at least some of the above-mentioned problems associated with production of C1 to C3 hydrocarbons has been discovered. One solution resides in utilizing a butane conversion unit (e.g., hydrocracking and/or hydrogenolysis unit) in combination with a separation unit and a distribution hub capable of distributing the hydrocarbons produced from the butane conversion unit to various downstream asset(s) (e.g., propylene production unit, ethylene production unit, methane reformation unit, etc.) in need of such hydrocarbons. Another solution resides in use of an isomerization unit which can produce an enriched n-butane feed from a mixed isobutane/n-butane feed by converting some of the isobutane to n-butane. The enriched n-butane feed stream can be provided to the butane conversion unit for further production of C2 and C3 hydrocarbons. In particular, the present invention can include a butane conversion unit which utilizes one or more hydrocracking and/or hydrogenolysis units capable of converting a butane-containing feed stream into a light alkane output stream including methane, ethane, and propane, in optional combinations with at least one isomerization unit capable of converting an isobutane-containing stream into a butane output stream including n-butane, a distribution network capable of receiving one or more of the separated individual streams and capable of distributing the individual streams to a downstream asset(s), or combinations thereof. In some embodiments, at least one separation unit capable of receiving at least part of the light alkane output stream and separating the components into individual streams is also combined with the butane conversion unit. In the present invention, a downstream asset can be a downstream processing unit and/or downstream production unit. Without wishing to be bound by theory, it is believed that the systems of the present invention allow for more effective use of the butane-containing feed, a better yield of ethane and propane, and a more cost efficient production process as the butane conversion unit operates independently of the downstream units and the isomerization of the isobutane to n-butane allows for use of a low value feed stock to produce a higher value product (e.g., C2 and C3 hydrocarbons). Furthermore, the distribution network is not dedicated to any specific downstream processing unit. Rather, the butane conversion unit produces products (e.g., methane, ethane, propane, hydrogen) that can then be supplied to multiple downstream processing units as needed through the distribution network. Thus, the system of the present invention can provide different feed streams to multiple downstream assets in a given region. Thus, the system can be tuned to provide products based on market conditions, which allows higher productivity for the chemical operations as no units are idle due to low demand of one or more products.

Further, while the distribution network configuration of the present invention can use any or all of the streams fed from the separation unit, in some aspects only the ethane stream and/or the propane stream may be used, which can increase the efficiency of the process from a cost and/or complexity perspective by focusing on the two components that are the most in demand in a commercial process (e.g., a petrochemical complex). Similarly, while the distribution network of the present invention can send the methane stream to downstream processes, in some aspects, the methane can be used as fuel for heating and/or the methane can be sent to a steam methane reformer for the production of hydrogen. Additional non-limiting advantages of the present invention can include (1) a fully integrated system configuration, (2) low operating costs, (3) use of low value feed stock (e.g., butane-containing streams) to generate ethane and propane, and/or (4) enhanced equipment performance through the use of the distribution network, which results in increased flexibility and efficiency in production of high value products (e.g., ethylene and propylene).

In one aspect of the present invention, systems for producing light alkanes for distribution and use are disclosed. A system can include a butane conversion unit, an isomerization unit, a separation unit fluidly coupled to the hydrocracking unit and/or the hydrogenolysis unit, and/or a distribution network fluidly coupled to the separation unit. The hydrocracking unit and/or the hydrogenolysis unit can be capable of converting a butane-containing feed stream to a light alkanes output stream containing methane ($CH_4$), ethane ($C_2H_6$), propane ($C_3H_8$), unreacted butane ($C_4H_{10}$). The isomerization unit can be capable of receiving at least a portion of the unreacted butane and converting isobutane in the unreacted butane stream to n-butane and recycling the n-butane and isobutane to the butane-containing feed stream sent to the butane conversion unit. The separation unit can be capable of receiving at least a portion of the light alkanes output stream and separating at least a portion of the light alkanes output stream into streams that include $CH_4$, $C_2H_6$, or $C_3H_8$. In some embodiments, the streams can comprise, consist essentially of, or consists of $CH_4$, $C_2H_6$, or $C_3H_8$. In some embodiments, the streams can include at least 50 vol. % to 100 vol. % $CH_4$, $C_2H_6$, or $C_3H_8$. In some embodiments, the streams can include other light alkanes. For example, the $CH_4$ stream can include up to 50% to 90 vol. % of $C_2H_6$ and/or $C_3H_8$ depending on the separation unit. The separation unit can include a distillation unit, a membrane unit, a de-propanizer, a de-ethanizer, a de-methanizer, a pressure swing adsorption unit, or any combination thereof. The isomerization unit can be capable of receiving at least a portion of a butane-containing stream leaving the separation unit, converting at least a portion of the isobutane in the butane-containing stream to n-butane, and recycling the stream leaving the isomerization unit to the butane conversion unit. The distribution network can include an input section and an output section and is not dedicated to any specific downstream processing unit(s) such that the distribution network operates independently from the downstream processing unit(s) but is capable of providing streams of $CH_4$, $C_2H_6$, and/or $C_3H_8$ to the downstream processing unit(s) as needed. The butane conversion unit may also output $C_4H_{10}$ and/or $H_2$ as unreacted reactants, but these will not be sent in concentrated streams to the downstream processing unit(s). Unreacted reactants may be recycled back to the feedstock. The distribution network can be operated independently and/or without knowledge of the operating conditions of the downstream processing unit(s). Similarly, the butane conversion unit is not dedicated to the downstream processing unit(s): the operating conditions of the butane conversion unit are designed to output $CH_4$, $C_2H_6$, and/or $C_3H_8$, but do not have to be designed to produce such products for a specific downstream processing unit(s). The butane conversion unit can be operated independently and/or without knowledge of the operating conditions of the downstream processing unit(s). The input section can be operable to receive one or both of (i) at least a portion of the $C_2H_6$ stream and (ii) at least a portion of the $C_3H_8$ stream from the separation unit. The output section can be operable to distribute one or both of (i) the at least a portion of the $C_2H_6$ stream and/or (ii) the at least a portion of the $C_3H_8$ stream. In some instances, the butane-containing feed stream can include at least 90 vol. % butanes. In some instances, the system can also include a butane separation unit fluidly coupled to the butane conversion unit, and a reverse isomerization unit fluidly coupled to the butane separation unit. The butane separation unit can be capable of producing a n-butane feed stream and an isobutane feed stream from a crude butane-containing feed stream, and providing the n-butane feed stream to the butane conversion unit. The reverse isomerization unit can be capable of receiving the isobutane feed stream and producing an n-butane/isobutane feed stream and providing the n-butane/isobutane feed stream to the butane separation unit. In some instances, the light alkanes output stream also includes isobutane. In such cases, the separation unit can be capable of producing an isobutane stream, and the system can include a reverse isomerization unit fluidly coupled to the separation unit. The n-butane/isobutane feed stream produced from the reverse isomerization unit can be provided to the butane conversion unit.

In some instances, the distribution network can include a $CH_4$ storage unit, a $C_2H_6$ storage unit, and/or a $C_3H_8$ storage unit, with each storage unit fluidly coupled to the input section and the output section of the distribution network. In some aspects, the storage unit can be portable. In some instances, at least one of the $CH_4$, $C_2H_6$, and/or $C_3H_8$ and storage units can be coupled to a ground transportation vessel, an ocean-going vessel, a river-going vessel, a pipeline, or any combination thereof. The distribution network input section, the distribution network output section, or both, can include a $CH_4$ storage pipeline, a $C_2H_6$ storage pipeline, and/or a $C_3H_8$ storage pipeline. The output section can be configured to distribute at least two of the $CH_4$, $C_2H_6$, and $C_3H_8$ streams to the same downstream processing unit.

In another aspect of the present invention systems for enriching butane streams with n-butane are described. A system can include a butane separation unit fluidly coupled to the butane conversion unit, and a reverse isomerization unit fluidly coupled to the butane separation unit. The butane separation unit can be capable of producing a n-butane feed stream and an isobutane feed stream from a crude butane-containing feed stream, and providing the n-butane feed stream to the butane conversion unit. The reverse isomerization unit can be capable of receiving the isobutane feed stream and producing an n-butane/isobutane feed stream and providing the n-butane/isobutane feed stream to the butane separation unit.

Another n-butane enrichment system can include a butane conversion unit fluidly coupled to both an alkane separation unit and a reverse isomerization unit. The butane conversion unit can be capable of converting a butane-containing feed stream to a light alkanes output stream containing methane ($CH_4$), ethane ($C_2H_6$), propane ($C_3H_8$), unreacted butane ($C_4H_{10}$). In some embodiments, the reverse isomerization unit is fluidly coupled to the butane conversion unit. The alkane separation unit can be capable of producing a mixed isobutane/n-butane stream from the unreacted $C_4H_{10}$ and providing the mixed isobutane/n-butane stream to the reverse isomerization unit. The isomerization unit can be capable of increasing the amount of n-butane in the mixed isobutane/n-butane stream and providing the enriched n-butane stream to the butane conversion unit. In some embodiments, the stream provided to the isomerization unit is obtained from another butane producing unit.

Also disclosed in the context of the present invention are processes for producing and distributing an ethane stream and a propane stream from a butane-containing feed stream. A process can include (a) hydrocracking or hydrogenolysis of the butane-containing feed stream to produce a light alkanes output stream that includes $CH_4$, $C_2H_6$, and $C_3H_8$, (b) separating at least a portion of the light alkanes output stream into streams that include $CH_4$, $C_2H_6$, and $C_3H_8$, and (c) distributing at least a portion of the separated $C_2H_6$ stream, at least a portion of the separated $C_3H_8$ stream, or both, to one or more downstream processing units. In some instances, the downstream processing units are not a dedicated $C_2H_6$ processing unit and/or a dedicated $C_3H_8$ processing unit. The process can also include distributing at least a portion of the separated $CH_4$ stream to a steam methane reforming unit and reforming the separated $CH_4$ stream to produce a steam methane reforming $H_2$-containing output stream. In some aspects, the process can also include distributing at least a portion of the steam methane reforming $H_2$ output stream to the hydrocracking or hydrogenolysis reaction. The separated $C_2H_6$ stream and/or the separated $C_3H_8$ stream can be distributed to the same downstream processing unit. At least a portion of the $CH_4$, $C_2H_6$, and/or $C_3H_8$ streams can be collected prior to distribution. In some instances, at least a portion of each of the separated $CH_4$, $C_2H_6$, and $C_3H_8$ streams can be distributed to one or more different downstream processing units at a different location than the downstream processing units already described in the distributing step (c). The process can further include: (i) separating a crude butane-containing feed stream that includes isobutane and n-butane into an isobutane feed stream and a n-butane feed stream, and optionally, the step (i) n-butane feed stream is the butane-containing stream of step (a); (ii) converting at least a portion of the isobutanes in the isobutane feed stream to n-butane/isobutane stream; (iii) providing the step (i) n-butane feed stream to the butane-containing feed stream of step (a); and (iv) providing n-butane/isobutane stream to step (i). In some embodiments, the light alkanes output stream can also include isobutane and the separation step (b) can produce an isobutane-containing stream. In such embodiments, the process can further include converting at least a portion of the isobutane in the isobutane-containing stream to n-butanes and producing an additional n-butane feed stream, and providing the additional n-butane feed stream to the butane-containing feed stream of step (a).

In another aspect of the present invention, a process for produce light alkanes from a butane-containing can include (a) separating a crude butane-containing feed stream that includes isobutane and n-butane into a isobutane-containing feed stream and a n-butane-containing feed stream, (b) converting at least a portion of the isobutane in the isobutane-containing feed stream to produce a n-butane/isobutane stream and (c) converting the n-butane feed stream from step (a), step (b), or both to a light alkanes stream that includes $CH_4$, $C_2H_6$, and $C_3H_8$. In a preferred instance, n-butane feed stream from step (a) and step (b) are both converted to the light alkanes stream. The light alkanes stream can be separated into streams that include $CH_4$, $C_2H_6$, and $C_3H_8$ and provided to a distribution unit where they can be distributed to downstream units independent of the butane conversion unit.

In another aspect of the present invention, another process for producing light alkanes from a butane-containing feed stream is described. A process can include (a) converting the butane-containing feed stream to a light alkanes stream that includes $CH_4$, $C_2H_6$, $C_3H_8$, and unreacted $C_4H_{10}$, (b) separating at least a portion of the light alkanes stream into streams that include $CH_4$, $C_2H_6$, $C_3H_8$, and unreacted butane ($C_4H_{10}$) that includes isobutane, and (c) converting a least of portion of the isobutane in the unreacted $C_4H_{10}$ to n-butane to produce a mixed isobutane/n-butane stream. The light alkanes stream can be separated into streams that include $CH_4$, $C_2H_6$, and $C_3H_8$ and provided to a distribution unit where they can be distributed to downstream units independent of the butane conversion unit.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %," "vol. %," or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, includes any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The processes and systems of the present invention can "comprise," "consist essentially of," or "consist of" particular ingredients, components, compositions, etc., disclosed throughout the specification. With respect to the phrase "consisting essentially of," a basic and novel characteristic of the present invention is the production of ethane and propane by using a distribution hub that is capable of receiving multiple product streams (e.g., ethane, propane, hydrogen streams) and providing those streams to regions of need. The distribution network can operate independently from the downstream processing unit(s) but is capable of providing the product streams to the downstream processing unit(s) as needed. The butane conversion unit can operate independently from the downstream processing unit(s). The distribution network and/or the butane conversion unit can be operated independently and/or without knowledge of the operating conditions of the downstream processing unit(s).

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings.

DETAILED DESCRIPTION OF THE INVENTION

A solution to at least some of the problems associated with production of ethylene and propylene from butane-containing streams by utilizing production of paraffins and distribution of said paraffin streams to olefin production units and other downstream units where paraffin streams are useful is described. The systems and processes of the present invention provide flexible distribution of paraffin streams as compared to current commercial practice of using dedicated cracking units having operating conditions that are dedicated for producing feed streams for a dedicated downstream processing unit (e.g., a butane hydrocracker that is dedicated to produce ethane for an ethane dehydrogenation unit with C3 being a by-product or a butane hydrocracker that is dedicated to produce propane for a propane dehydrogenation unit with C2 being a by-product, etc.). Thus, the systems and processes of the present invention can maximize butane hydrocracking and then distribute, as needed or desired, the cracked products (ethane, butane, methane, etc.) to downstream processing units. In this way, the butane hydrocracking and/or hydrogenolysis units of the present invention as well as the distribution network operate independently/are not dedicated to a given downstream processing unit. It is believed that this setup can result in maximization of efficiency and production of valuable feed streams.

It has also been discovered in the context of the present invention that a hydrocracker or hydrogenolysis unit with the capability to utilize a butane feed stream can improve the efficiency, distribution, and use of the produced light alkane products because there are fewer products to separate, the temperature and pressure conditions required for hydrocracking butane are not as extreme as those for hydrocracking heavier hydrocarbons, and refineries often have available butane stock.

These and other non-limiting aspects of the present invention are discussed in further detail in the following sections with reference to FIGS. 1-5. In FIGS. 1-5, units can include one or more heating and/or cooling devices (e.g., insulation, electrical heaters, jacketed heat exchangers in the wall) or controllers (e.g., computers, flow valves, automated values, etc.) that can be used to control temperatures and pressures of the processes. While only one unit is usually shown, it should be understood that multiple units can be housed in one unit.

Figure 1:
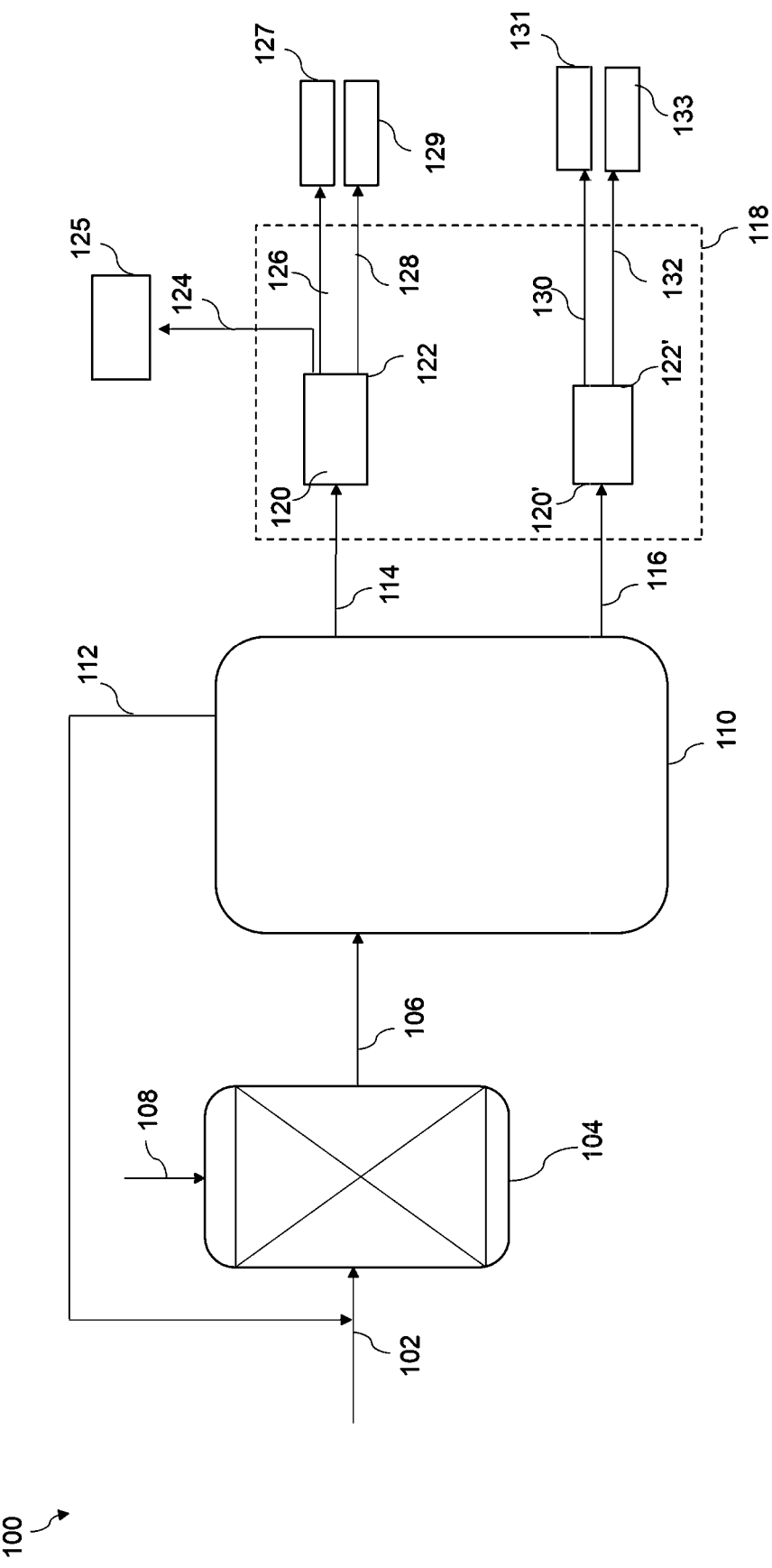
FIG. 1 shows a schematic diagram of a system of the present invention for producing light alkanes for distribution and use, according to an embodiment of the invention where a hydrocracking unit supplies methane, ethane, propane, and hydrogen to a separation unit, which separates the ethane and propane into separate streams to send to a distribution unit.

Systems and processing for producing light alkanes for distribution and use include a butane conversion unit which can include at least one hydrocracking unit and/or hydrogenolysis unit, a separation unit, and a distribution network that includes an input section and an output section. With reference to FIG. 1, a schematic diagram is shown of system 100 that is capable of producing light alkanes for distribution and use with a more flexible system, lower operating costs, efficient use of butane, and/or more effective use of resources compared to conventional methods. System 100 can include butane conversion unit 104, separation unit 110, and distribution unit 118. In one instance unit 104 is a hydrocracking unit. In another instance unit 104 is a hydrogenolysis unit. In some embodiments, there can be multiple units 104 and at least one can be a hydrocracking unit and at least one can be a hydrogenolysis unit. Hydrocracking unit and/or hydrogenolysis unit can be used interchangeably throughout this specification unless indicated otherwise. In system 100, C4 hydrocarbon stream 102 that includes butane can enter butane conversion unit 104. Butane-containing stream 102 can include 90 vol. % butanes or at least 90 vol. %, 91 vol. %, 92 vol. %, 93 vol. %, 94 vol. %, 95 vol. %, 96 vol. %, 97 vol. %, 98 vol. %, or at least 99 vol. %, or any range or value there between. In hydrocracking unit 104, butane can be converted to a light alkanes output stream 106 through a hydrocracking reaction and/or a hydrogenolysis reaction. Light alkanes output stream 106 can include methane ($CH_4$), ethane ($C_2H_6$), and propane ($C_3H_8$). In some instances, output stream 106 can also contain unreacted butane ($C_4H_{10}$), and unreacted hydrogen ($H_2$), benzene, toluene, xylenes, BTX byproducts, and/or other heavy hydrocarbons (C5+). As shown, hydrogen stream 108 can enter hydrocracking unit 104 to ensure enough hydrogen exists for the hydrocracking or hydrogenolysis to take place. In some embodiments, the make-up hydrogen stream comprises at least 2 vol. % hydrogen. In some embodiments, $H_2$ streams used by the systems or processes of the present invention can include at least 90 vol. % $H_2$. In some embodiments, hydrogen stream 108 is not necessary. In embodiments of the invention, the C4 hydrocarbon feed stream 102 can be purified by flowing the feed stream through a filter or guard bed to reduce impurities therefrom (not shown). Filtration of impurities in streams can increase productivity in the process by reducing fouling or poisoning of the catalyst in the butane conversion unit.

In some embodiments of the invention, butane conversion unit 104 is a single-stage hydrocracking unit. In some embodiments, hydrocracking unit 104 is a multiple-stage hydrocracking unit. In some embodiments of the invention, the hydrocracking unit can have at least one fixed-bed reactor in which the butane-containing feed stream and hydrogen flow over catalytic beds. In some embodiments of the invention, the hydrocracking unit operates at pressure ranges of 50 psi to 250 psi (3 bar to 18 bar). In some embodiments of the invention, the hydrocracking unit operates at temperatures in the range of 350° C. to 600° C. Non-limiting examples of a hydrocracking catalyst that can be used in hydrocracking unit 104 include platinum group metal (e.g., iridium (Ir), platinum (Pt), osmium (Os) and the like) catalysts, amorphous silica-alumina (ASA) and/or zeolitic cracking catalysts. Conditions and catalysts in the butane conversion unit 104 can be determined by a person of skill in hydrocracking (e.g., a chemical engineer). In this setup, the butane conversion unit(s) 104 can operate independently from downstream processing units (e.g., propylene production unit, ethylene production unit, methane reformation unit, etc.) that process the produced light alkanes. By operating independently, unit(s) 104 does not have to be dedicated such that its operating conditions are designed to produce a particular light alkane; rather unit(s) 104 can be designed to produce light alkane stream 106, which can then be separated and distributed as needed or desired to a variety of downstream processing units (not shown).

In some embodiments of the invention, butane conversion unit 104 is a hydrogenolysis unit. In some embodiments of the invention, hydrogenolysis unit 104 includes a hydrogenation unit. In some embodiments of the invention, the hydrogenolysis unit can have at least one fixed-bed reactor in which the butane-containing feed stream and hydrogen flow over catalytic beds. In some embodiments of the invention, the hydrogenolysis unit can have at least one batch reactor in which the butane-containing feed is placed in the reactor, the catalyst is suspended in the feed, and hydrogen is introduced at pressure. In some embodiments of the invention, the hydrogenolysis unit operates at pressure ranges of 50 psi to 250 psi (3 bar to 18 bar). In some embodiments of the invention, the hydrogenolysis unit operates at temperatures in the range of 200° C. to 400° C. Non-limiting examples of a hydrogenolysis catalyst that can be used in hydrogenolysis unit 104 include nickel, platinum, iridium, rhodium, tungsten, ruthenium, palladium, ruthenium, copper chromite, kieselguhr, the oxides of nickel, platinum, palladium, and ruthenium, and combinations thereof. The above metals can be supported on aluminas, silicas, silicaaluminas, titania, zeolites, SAPOs, A1POs, etc. Conditions and catalysts in the hydrogenolysis unit 104 can be determined by a person of skill in hydrogenolysis (e.g., a chemical engineer).

Light alkanes output stream 106 can exit butane conversion unit 104 and enter separation unit 110. Light alkanes output stream 106 can include methane, ethane, propane, optionally unreacted butane, and optionally unreacted hydrogen. Separation unit 110 can receive at least a portion of the light alkanes output stream and separate at least a portion of the light alkanes output stream into streams that include primarily or least 10 vol. % to 100 vol. % methane, ethane, and propane. Non-limiting examples of separation unit(s) can include a distillation unit, a membrane unit, a de-propanizer, a de-ethanizer, a de-methanizer, a pressure swing adsorption unit, or combinations thereof. In separation unit 110, light alkanes output stream 106 is separated into recycle stream 112, ethane-containing stream 114 and propane-containing stream 116. Recycle stream 112 can optionally include hydrogen and can be recycled back to butane-containing feed stream 102 and/or sent directly to hydrocracking unit/hydrogenolysis unit 104 (not shown). In embodiments of the invention, recycle stream 112 can include at least 90 vol. % hydrogen, or 90 to 100 vol. % hydrogen. At startup of butane conversion 104, recycle stream 112 does not combine with butane-containing feed stream 102 because no product has been produced. Until operating conditions are achieved, the composition of butane-containing feed stream 102 as it enters butane conversion unit 104 can change as more of recycle stream 112 is added and steady state operation is achieved. In some embodiments of the invention, recycle stream 112 can be recycled to another unit that needs methane and hydrogen (not shown). In some embodiments of the invention, no portion of stream 112 is recycled (not shown). In some embodiments of the invention, separation unit 110 can separate stream 106 into at least four streams including a hydrogen-containing stream, a methane-containing stream, an ethane-containing stream, and a propane-containing stream (not shown). In some embodiments, each of the streams exiting separation unit 110 enter distribution unit 118 to be sent or stored as needed (not shown). In some embodiments of the invention, stream 116 also contains butane and/or heavy hydrocarbons (C5+). In some embodiments, separation unit 110 includes at least two distillation columns, condensers, and/or other methods of separation known in the industry to separate methane, ethane, propane, butane, heavy hydrocarbons, and/or hydrogen (not shown).

Ethane-containing stream 114 and propane-containing stream 116 can both exit separation unit 110 and enter distribution unit 118. In embodiments of the invention, stream 114 can include 90 to 100 vol. % ethane. In embodiments of the invention, stream 116 can include 90 to 100 vol. % propane. In some embodiments, separation unit 110 can produce a combined ethane- and propane-containing stream, which can be sent to distribution unit 118 for distribution to downstream units that can use a combined stream. In some embodiments, separation unit 110 can separate the product stream 106 into at least four individual streams: a methane-containing stream, a hydrogen-containing stream, an ethane-containing stream, and a propane-containing stream (not shown). In some embodiments of the invention, the separated hydrogen-containing stream contains at least 90 vol. % hydrogen or 90 to 100 vol. % hydrogen or any range or value there between. Separated methane-containing stream contains at least 90 vol. % methane or 90 to 100 vol. % methane or any value or range there between. Separated ethane-containing stream contains at least 90 vol. % ethane, or 90 to 100 vol. % ethane or any value or range there between. Propane-containing stream contains at least 90 vol. % propane or 90 to 100 vol. % propane or any value or range there between.

In embodiments of the invention, distribution network 118 can include at least one input section and at least one output section and is not dedicated to any specific downstream processing unit. Input section can receive at least a portion of the ethane stream and/or at least a portion of the propane stream from the separation unit and output section can distribute the at least a portion of the ethane stream and/or the at least a portion of the propane stream. The input section and/or output section can include valves, a storage tank, a transportation vessel, an ocean-going vessel, a river-going vessel, or any combination thereof or the like. As shown, distribution unit 118 includes an ethane input section 120, a propane input section 120', an ethane output section 122, and a propane output section 122'. Non-limiting examples of input sections 120, 120' and/or output sections 122, 122' can include an ethane storage unit and a propane storage unit, respectively. Although not shown, methane and hydrogen storage units can be used when such streams are produced and separated. In some embodiments of the invention, the input section 120 and 120' of distribution unit 118 are valves or storage units and are coupled to output section 122, or 122', respectively. By way of example, output section 122, 122' can be a methane pipeline, an ethane pipeline, and/or a propane pipeline. In some embodiments, the distribution unit 118 can distribute at least two of the streams entering the distribution unit to the same downstream processing unit or storage warehouse which is capable of receiving more than one stream. In those instances, distribution unit 118 can send the streams to downstream units as needed for the operations being run at different parts of a plant and or be distributed to an offsite facility. By means of distribution network 118, products from separation unit 110 can be provided to one or more sites as necessary. By way of example, ethane stream 114 can enter input section 120 of distribution unit 118 and exit the distribution unit to downstream process unit 125 requiring ethane via output conduit 124, ethane furnace 127 via output conduit 126, and storage unit 129 via output conduit 128. Propane feedstock 116 can enter input section 120' of distribution unit 118 and exit the distribution unit (e.g., a storage vessel) to propane dehydrogenation (PDH) unit 131 via output conduit 130, and/or storage unit 133 via output conduit 132. In this setup, the distribution unit 118 can operate independently from downstream processing units (e.g., propylene production unit, ethylene production unit, methane reformation unit, etc.) that process the produced light alkanes. By operating independently, distribution unit 118 does not have to be dedicated such that its operating conditions are designed to distribute a particular light alkane; rather distribution unit 118 can be designed to distribute methane, ethane, propane, and/or hydrogen as needed or desired to a variety of downstream processing units.

In some instances, a methane containing stream (not shown) exits distribution system 118 and enter a methane steam reforming unit. In a methane steam reforming unit, the methane can be reformed (e.g., dry reformed, steam reformed, or both) to produce a hydrogen ($H_2$) containing stream. The $H_2$-containing stream can be provided to butane conversion unit 104. In a preferred embodiment, the $H_2$-containing stream is provided to a hydrogenolysis unit.

In some embodiments of the invention, distribution unit 118 can also receive at least a portion of each separated methane stream, one or more mixed streams of methane, ethane, propane, butane, and/or hydrogen or combinations thereof from the butane conversion unit 104 in the current invention or another unit in another unit not mentioned in this invention (not shown). In some embodiments of the invention, the distribution unit 118 can include one or more purification units or systems.

Figure 2:
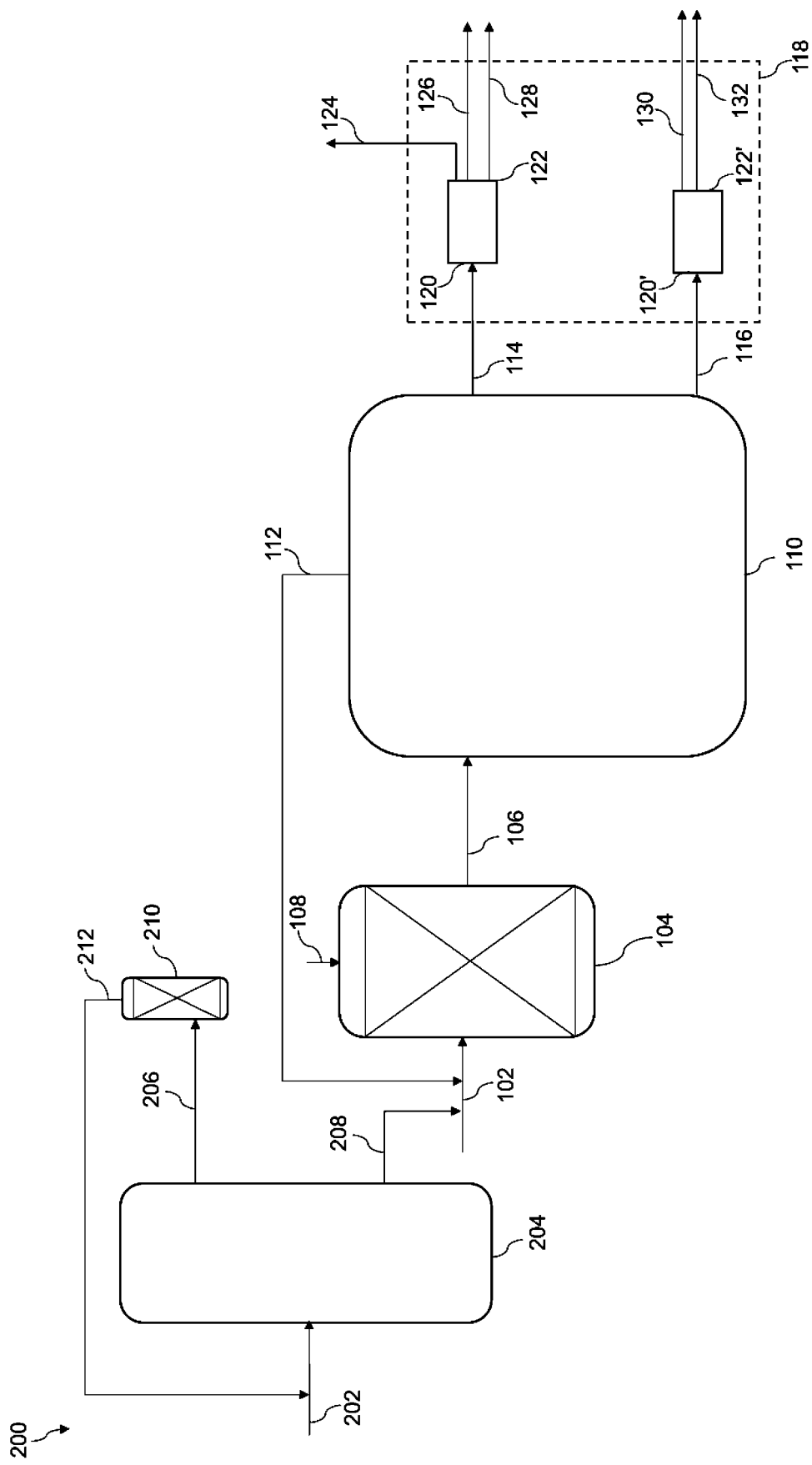
FIG. 2 shows a schematic diagram of another system of the present invention that includes a butane separation coupled to a butane conversion unit, and a reverse isomerization unit fluidly coupled to the butane separation unit.

In some embodiments of the invention a crude butane feed stream can include isobutane and butane. Separation of the isobutane from the butane can be desirable as conversion of isobutane to light alkanes in the butane conversion unit can be minimal or low. By way of example, a hydrogenolysis catalyst can be selective for n-butane conversion and not selective for isobutane conversion. Referring to FIG. 2, a butane separation unit can be fluidly coupled to the butane conversion unit 104, and a reverse isomerization unit fluidly coupled to the butane separation unit. The butane separation unit can produce a n-butane feed stream and an isobutane feed stream from a crude butane-containing feed stream. Separation of the isobutane followed by conversion to n-butane provides a more efficient process as all or substantially all of the crude-butane feed is converted to light alkanes. With reference to FIG. 2, a crude butane-containing feed stream 202 enters a butane separation unit 204 and isobutane-containing stream 206 and n-butane-containing stream 208 leave butane separation unit 204.

In some embodiments, the butane separation unit 204 can contain at least one distillation column (not shown). Butane separation unit 204 can contain any separation unit known in the art. In some embodiments, isobutane-containing stream 206 can be sent to a reverse isomerization unit 210. In some embodiments of the invention, isobutane-containing stream 206 can include 70 to 100 vol. % isobutane and 0 to 30 vol. % n-butane, or at least 70 vol. %, 75 vol. %, 80 vol. %, 85 vol. %, 90 vol. %, 95 vol. %, or 100 vol. % isobutane, and 0 vol. %, 5 vol. %, 10 vol. %, 15 vol. %, 20 vol. %, 25 vol. %, or 30 vol. % n-butane, or any range or value there between.

In some embodiments, n-butane-containing stream 208 is combined with butane feed stream 102. In some embodiments of the invention, n-butane-containing stream 208 includes 70 to 100 vol. % n-butane and 0 to 30 vol. % isobutane, or at least 70 vol. %, 75 vol. %, 80 vol. %, 85 vol. %, 90 vol. %, 95 vol. %, or 100 vol. % n-butane, and 0 vol. %, 5 vol. %, 10 vol. %, 15 vol. %, 20 vol. %, 25 vol. %, or 30 vol. % isobutane, or any range or value there between. In some embodiments of the invention, n-butane-containing stream 208 enters butane conversion unit 104 without contacting feed stream 102 (not shown). In some embodiments of the invention, n-butane-containing stream 208 is feed stream 102 and no other components are added.

In some embodiments of the invention, isobutane-containing stream 206 enters reverse isomerization unit 210. The reverse isomerization unit can convert the isobutane feed stream to produce n-butane/isobutane stream 212. The n-butane/isobutane stream 212 can be recycled to the butane separation unit 404. In some embodiments, the reverse isomerization unit contains a reactor which converts at least some of the isobutane entering the unit to n-butane by rearranging the carbon-carbon bonds in the presence of a catalyst. In some embodiments of the invention, mixture stream 212 can include 40 to 60 vol. % isobutane and 40 to 60 vol. % n-butane, or at least 40 vol. %, 45 vol. %, 50 vol.

%, 55 vol. %, 60 vol. % isobutane, and at least 40 vol. %, 45 vol. %, 50 vol. %, 55 vol. %, 60 vol. % n-butane, or any range or value there between. In some embodiments, the temperature of the reverse isomerization unit is in the range of 150° C. to 600° C., or at least 150° C., 200° C., 250° C., 300° C., 350° C., 400° C., 450° C., 500° C., 550° C., 600° C., or any range or value there between. In some embodiments of the invention, at least a portion of stream 212 is recycled to combine with n-butane-containing feed stream 202.

Figure 3:
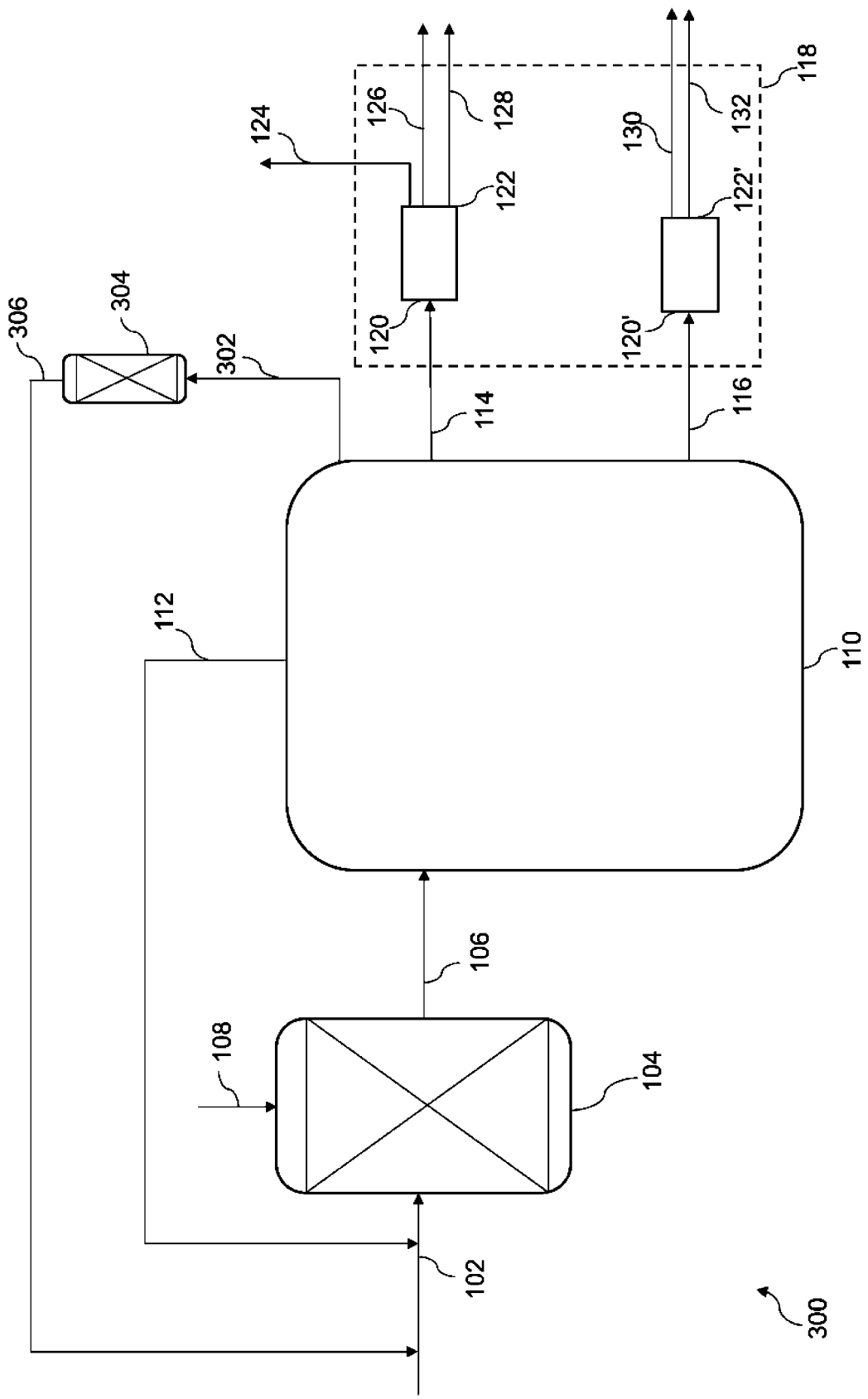
FIG. 3 shows a schematic diagram of another system of the present invention that includes a reverse isomerization unit fluidly coupled to a separation unit.

In some instances, the light alkanes output stream exiting the butane conversion unit also includes isobutane. In such cases, the separation unit can be capable of producing an isobutane stream, and the system can include a reverse isomerization unit fluidly coupled to the separation unit. With reference to FIG. 3, a reverse isomerization unit 304 can convert isobutane-containing stream 302 exiting the separation unit 110 to a mixture of isobutane and n-butane, which exits the reverse isomerization unit as stream 306. In some embodiments, the n-butane/isobutane stream 306 can be recycled to the crude butane feed 102 and/or the butane conversion unit 104.

In some embodiments, separation of methane, ethane, propane, unreacted butane, and/or unreacted hydrogen from stream 106 is performed in one or more condensers (not shown). In some embodiments of the invention, butane separation unit 204 is at least one condenser (not shown). In some embodiments of the invention, the separation unit 110 includes at least two distillation columns in series (not shown).

Figure 4:
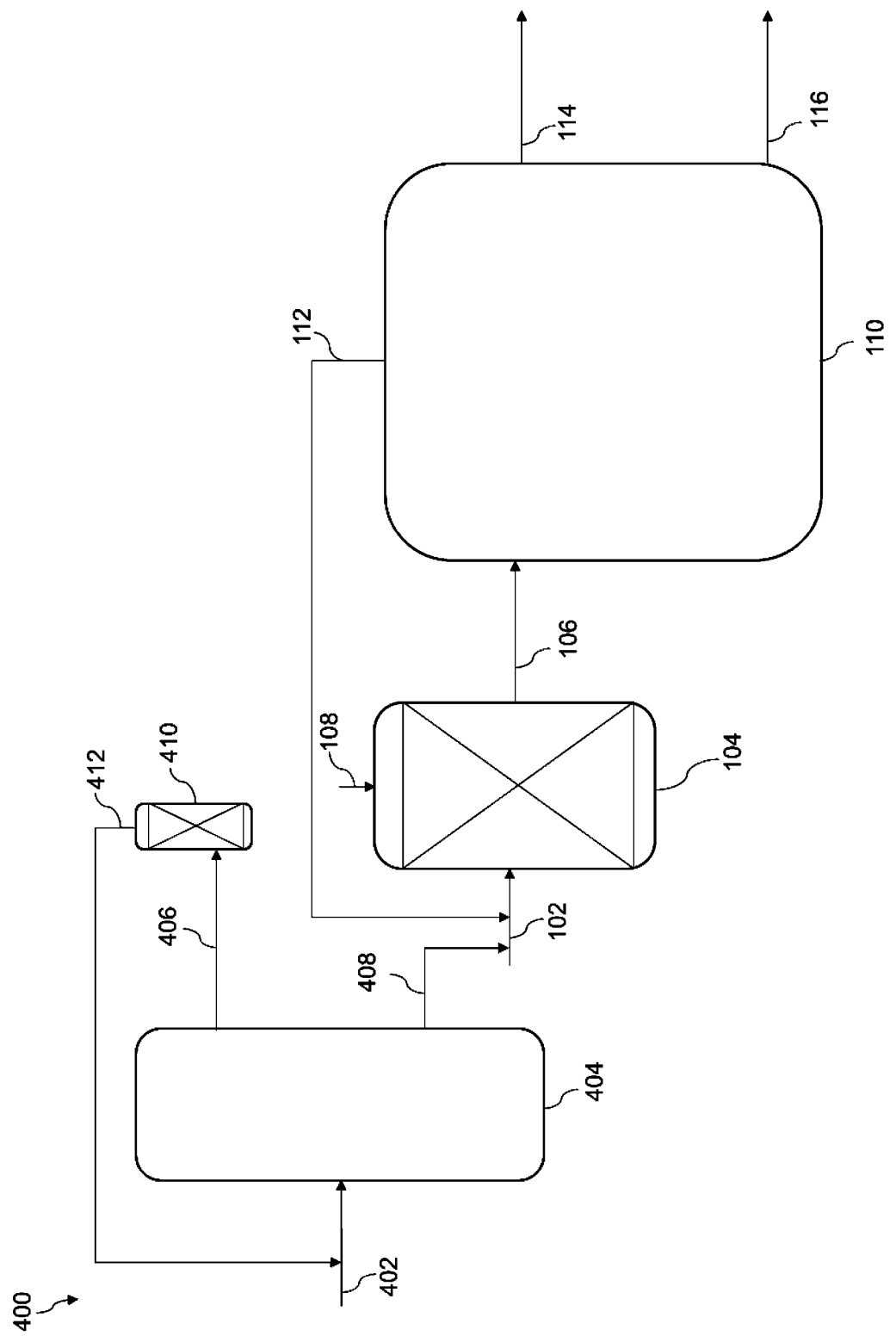
FIG. 4 shows a schematic diagram of another system of the present invention that includes a butane separation coupled to a butane conversion unit, a reverse isomerization unit fluidly coupled to the butane separation unit, a butane conversion unit, and a separation unit fluidly coupled to the butane conversion unit.

In some embodiments of the invention, a butane separation unit can be fluidly coupled to butane conversion unit 104, and a reverse isomerization unit fluidly coupled to butane separation unit with no distribution network in the system. The butane separation unit can produce a n-butane feed stream and an isobutane feed stream from a crude butane-containing feed stream. With reference to FIG. 4, a crude butane-containing feed stream 402 enters a butane separation unit 404. Butane separation unit 404 can contain any separation unit known in the art. In some embodiments, the butane separation unit 404 can contain at least one distillation column (not shown). In some embodiments, most of the isobutane and some of the n-butane exit butane separation unit 404 as isobutane-containing stream 406 and most of the n-butane and some of the isobutane exit butane separation unit 404 as n-butane-containing stream 408.

In some embodiments, isobutane-containing stream 406 can be sent to a reverse isomerization unit 410. In some embodiments of the invention, isobutane-containing stream 406 can include 70 to 100 vol. % isobutane and 0 to 30 vol. % n-butane, or at least 70 vol.%, 75 vol. %, 80 vol. %, 85 vol. %, 90 vol. %, 95 vol. %, or 100 vol. % isobutane, and 0 vol. %, 5 vol. %, 10 vol. %, 15 vol. %, 20 vol. %, 25 vol. %, or 30 vol. % n-butane, or any range or value there between.

In some embodiments, n-butane-containing stream 408 is sent to mix with butane feed stream 102. In some embodiments of the invention, n-butane-containing stream 408 includes 70 to 100 vol. % n-butane and 0 to 30 vol. % isobutane, or at least 70 vol. %, 75 vol. %, 80 vol. %, 85 vol. %, 90 vol. %, 95 vol. %, or 100 vol. % n-butane, and 0 vol. %, 5 vol. %, 10 vol. %, 15 vol. %, 20 vol. %, 25 vol. %, or 30 vol. % isobutane, or any range or value there between. In some embodiments of the invention, n-butane-containing stream 408 enters butane conversion unit 104 without contacting feed stream 102 (not shown). In some embodiments of the invention, n-butane-containing stream 408 is feed stream 102 and no other components are added.

In some embodiments of the invention, isobutane-containing stream 406 enters reverse isomerization unit 410. The reverse isomerization unit can convert the isobutane feed stream to produce n-butane/isobutane stream 412. The n-butane/isobutane stream 412 can be recycled to the butane separation unit 404. In some embodiments, the reverse isomerization unit contains a reactor which converts at least some of the isobutane entering the unit to n-butane by rearranging the carbon-carbon bonds in the presence of a catalyst. In some embodiments of the invention, mixture stream 412 can include 40 to 60 vol. % isobutane and 40 to 60 vol. % n-butane, or at least 40 vol. %, 45 vol. %, 50 vol. %, 55 vol. %, 60 vol. % isobutane, and at least 40 vol. %, 45 vol. %, 50 vol. %, 55 vol. %, 60 vol. % n-butane, or any range or value there between. In some embodiments, the temperature of the reverse isomerization unit is in the range of 150° C. to 600° C., or at least 150° C., 200° C., 250° C., 300° C., 350° C., 400° C., 450° C., 500° C., 550° C., 600° C., or any range or value there between. In some embodiments of the invention, at least a portion of stream 412 is recycled to combine with n-butane-containing feed stream 402.

In some embodiments, ethane-rich stream 114 exits separation unit 110 to be sent to a downstream processing unit to create ethylene, a storage unit, or sold as a product. In some embodiments, propane-rich stream 116 exits separation unit 110 to be sent to a downstream processing unit to create propylene, a storage unit, or sent as a product.

Figure 5:
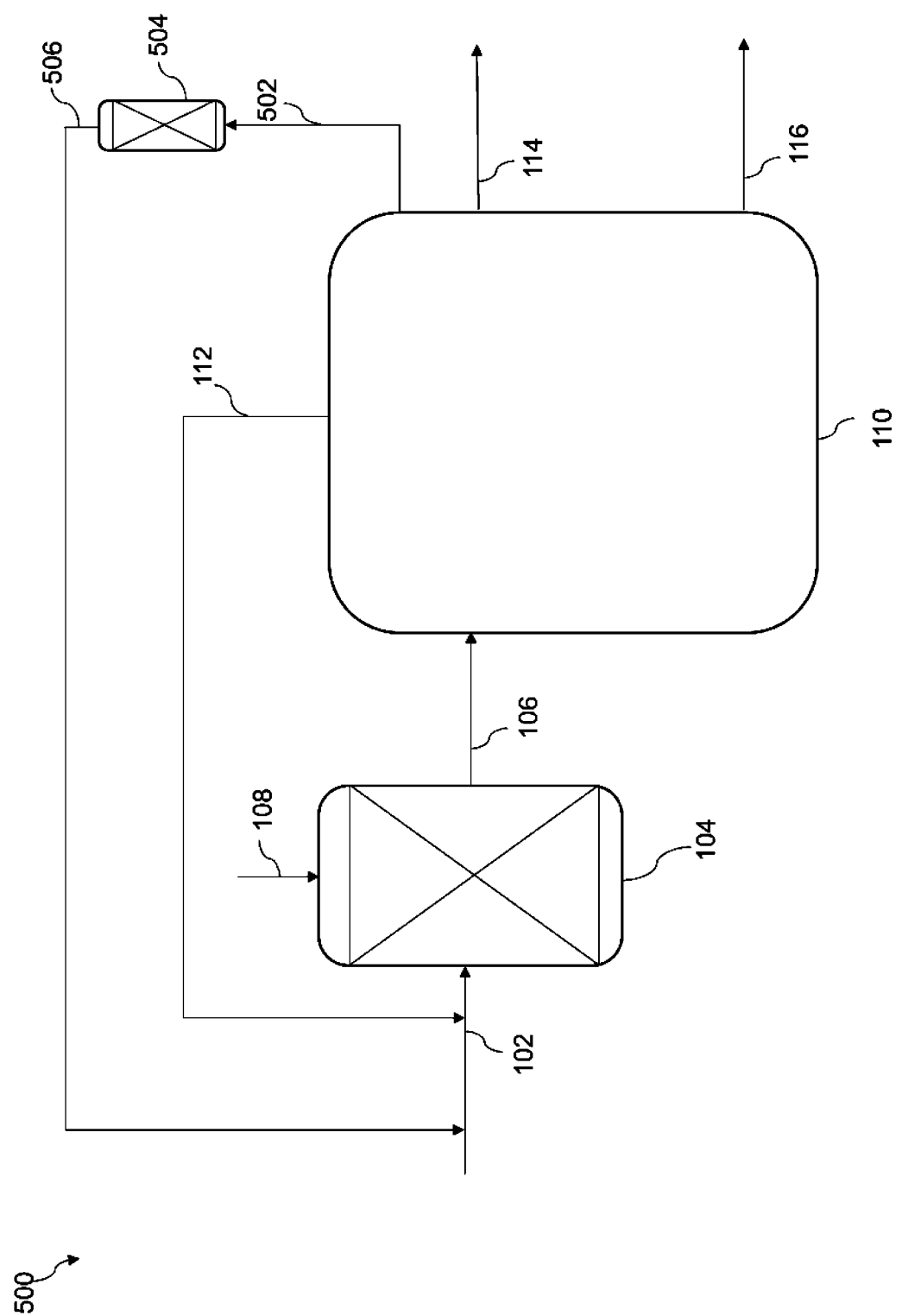
FIG. 5 shows a schematic diagram of another system of the present invention that includes a reverse isomerization unit fluidly coupled to a separation unit, which separates methane, ethane, propane, and hydrogen supplied from a butane conversion unit.

In some instances, the light alkanes output stream 106 exiting the butane conversion unit also includes isobutane. In such cases, separation unit 110 can be capable of producing an isobutane stream, and the system can include a reverse isomerization unit fluidly coupled to the separation unit not fluidly coupled to a distribution network. With reference to FIG. 5, a reverse isomerization unit 504 can convert isobutane-containing stream 502 exiting the separation unit 110 to a mixture of isobutane and n-butane, which exits the reverse isomerization unit as stream 506. In some embodiments, the n-butane/isobutane stream 506 can be recycled to the crude butane feed 102 and/or the butane conversion unit 104. In some embodiments, ethane-rich stream 114 exits separation unit 110 to be sent to a downstream processing unit to create ethylene, a storage unit, or sold as a product. In some embodiments, propane-rich stream 116 exits separation unit 110 to be sent to a downstream processing unit to create propylene, a storage unit, or sent as a product.

Although embodiments of the present invention have been described with reference to systems of FIGS. 1-5, it should be appreciated that operation of the present invention is not limited to the particular systems and/or processes, and/or the particular order of the systems illustrated in the figures. Accordingly, embodiments of the invention can provide functionality as described herein using various steps in a sequence different than that of the figures.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein can be utilized. Accordingly, the appended claims are intended to include within their scope such processes, machines, manufacture, compositions of matter, means, methods, or steps.

The invention claimed is:

1. A system for generating light alkanes for general distribution and use, the system comprising:
a butane conversion unit, the butane conversion unit capable of converting a butane-containing feed stream to a light alkanes output stream comprising methane ($CH_4$), ethane ($C_2H_6$), and propane ($C_3H_8$);
a separation unit fluidly coupled to the butane conversion unit, the separation unit capable of receiving at least a portion of the light alkanes output stream and separating at least a portion of the light alkanes output stream into streams comprising $CH_4$, $C_2H_6$, and $C_3H_8$; and
a distribution network fluidly coupled to the separation unit, the distribution network capable of receiving one or both of (i) at least a portion of the $C_2H_6$ stream and (ii) at least a portion of the $C_3H_8$ stream from the separation unit, and distributing one or both of (i) the at least a portion of the $C_2H_6$ stream or (ii) the at least a portion of the $C_3H_8$ stream, wherein the distribution network is not dedicated to any specific downstream processing unit;
wherein the butane conversion unit comprises a hydrocracking unit; and
wherein the butane conversion unit comprises a hydrogenolysis unit.

2. The system of claim 1, further comprising a steam methane reforming unit operable to:
receive at least a portion of the $CH_4$ stream from the separation unit and produce a steam methane reforming output stream comprising $H_2$; and
provide at least a portion of the steam methane reforming $H_2$ output stream to the butane conversion unit.

3. The system of claim 1, wherein the separation unit is further operable to provide at least a portion of the separated $H_2$ stream to the butane conversion unit.

4. The system of claim 1, wherein the separation unit comprises a distillation unit, a membrane unit, a propane separation unit, an ethane separation unit, a methane separation unit, a pressure swing adsorption unit, or any combination thereof.

5. The system of claim 1, wherein the distribution network comprises at least one of a $CH_4$ storage unit, a $C_2H_6$ storage unit a $C_3H_8$ storage unit, wherein at least one of the storage units is fluidly coupled to an input section and an output section of the distribution network.

6. The system of claim 5, wherein at least one of the $CH_4$, $C_2H_6$, $C_3H_8$ storage units, or any combination thereof is/are coupled to a ground transportation vessel, an ocean-going vessel, a river-going vessel, or any combination thereof, or at least a portion of the distribution network is a $CH_4$ pipeline, a $C_2H_6$ pipeline, and a $C_3H_8$ pipeline, or any combination thereof.

7. The system of claim 1, wherein the distribution network is capable of distributing at least two of the $CH_4$, $C_2H_6$, $C_3H_8$, and $H_2$ streams and/or a $C_4H_{10}$-rich stream to the same downstream processing unit.

8. The system of claim 1, further comprising:
a butane separation unit fluidly coupled to the butane conversion unit, the butane separation unit capable of producing a n-butane feed stream and an isobutane feed stream from a crude butane-containing feed stream, and providing the n-butane feed stream to the butane conversion unit; and
a reverse isomerization unit fluidly coupled to the butane separation unit, the reverse isomerization unit capable of receiving the isobutane feed stream and producing an n-butane/isobutane feed stream and providing the n-butane/isobutane feed stream to the butane separation unit.

9. The system of claim 1, wherein the light alkanes output stream further comprises isobutane, wherein the separation unit is further capable of producing a stream comprising isobutane, the system further comprising:
a reverse isomerization unit fluidly coupled to the separation unit, the reverse isomerization unit capable of receiving the isobutane stream and producing an isomerized stream comprising n-butane and isobutane, and providing the isomerized feed stream to the butane conversion unit.

10. The system of claim 1, wherein the hydrocracking unit comprises a hydrocracking catalyst.

11. The system of claim 1, wherein the hydrogenolysis unit comprises a hydrogenolysis catalyst.

12. A system for generating light alkanes for general distribution and use, the system comprising:
a butane conversion unit, the butane conversion unit capable of converting a butane-containing feed stream to a light alkanes output stream comprising methane ($CH_4$), ethane ($C_2H_6$), and propane ($C_3H_8$);
a separation unit fluidly coupled to the butane conversion unit, the separation unit capable of receiving at least a portion of the light alkanes output stream and separating at least a portion of the light alkanes output stream into streams comprising $CH_4$, $C_2H_6$, and $C_3H_8$; and
a distribution network fluidly coupled to the separation unit, the distribution network capable of receiving one or both of (i) at least a portion of the $C_2H_6$ stream and (ii) at least a portion of the $C_3H_8$ stream from the separation unit, and distributing one or both of (i) the at least a portion of the $C_2H_6$ stream or (ii) the at least a portion of the $C_3H_8$ stream,
wherein the distribution network is not dedicated to any specific downstream asset, wherein the downstream asset is selected from the group consisting of a downstream processing unit and a downstream production unit.

13. A system for generating light alkanes for general distribution and use, the system comprising:
a butane conversion unit, the butane conversion unit capable of converting a butane-containing feed stream to a light alkanes output stream comprising methane ($CH_4$), ethane ($C_2H_6$), and propane ($C_3H_8$);
a separation unit fluidly coupled to the butane conversion unit, the separation unit capable of receiving at least a portion of the light alkanes output stream and separating at least a portion of the light alkanes output stream into streams comprising $CH_4$, $C_2H_6$, and $C_3H_8$; and
a distribution network fluidly coupled to the separation unit, the distribution network capable of receiving one or both of (i) at least a portion of the $C_2H_6$ stream and (ii) at least a portion of the $C_3H_8$ stream from the separation unit, and distributing one or both of (i) the at least a portion of the $C_2H_6$ stream or (ii) the at least a portion of the C$_3$H$_8$ stream, wherein the distribution network is not dedicated to any specific downstream processing unit.

* * * * *